(12) United States Patent
Schwab et al.

(10) Patent No.: US 10,869,583 B2
(45) Date of Patent: Dec. 22, 2020

(54) WASH, CLEAN AND DRY SYSTEM WITH REMOVABLE SPRAY CANISTER DEVICE

(71) Applicant: Whole Bath, LLC, East Chatham, NY (US)

(72) Inventors: Brian Schwab, East Chatham, NY (US); Shao-Yu Peng, Changhua County (TW); Brian Murray, Albany, NY (US)

(73) Assignee: Whole Bath, LLC, East Chatham, NY (US)

( * ) Notice: Subject to any disclaimer, the term of this patent is extended or adjusted under 35 U.S.C. 154(b) by 0 days.

(21) Appl. No.: 15/650,957

(22) Filed: Jul. 16, 2017

(65) Prior Publication Data
US 2018/0028797 A1    Feb. 1, 2018

Related U.S. Application Data

(63) Continuation-in-part of application No. 15/588,635, filed on May 6, 2017, and a continuation-in-part of (Continued)

(51) Int. Cl.
*A61M 3/02* (2006.01)
*A61M 3/06* (2006.01)
(Continued)

(52) U.S. Cl.
CPC .............. *A47K 10/48* (2013.01); *A47K 13/24* (2013.01); *A61M 3/022* (2014.02);
(Continued)

(58) Field of Classification Search
CPC ....................................................... E03D 9/08
(Continued)

(56) References Cited

U.S. PATENT DOCUMENTS

| | | |
|---|---|---|
| 2,875,450 A | 3/1959 | Umann |
| D198,085 S | 4/1964 | Rich |

(Continued)

FOREIGN PATENT DOCUMENTS

| | | |
|---|---|---|
| CN | 101933781 | 1/2001 |
| CN | 201551648 | 8/2010 |

(Continued)

OTHER PUBLICATIONS

PCT Notification of Transmittal of The International Search Report and The Written Opinion of the International Searching Authority, or Declaration; PCT/US2017/031485, filed on May 6, 2017 by Whole Bath, LLC.
(Continued)

*Primary Examiner* — Lori L Baker
(74) *Attorney, Agent, or Firm* — Fitch, Even, Tabin & Flannery LLP (57) ABSTRACT

A method and a wash, clean and dry system are provided for washing, cleaning and drying a surface region of a human body. The system includes a toilet seat assembly with a bidet assembly having a spray canister device for spraying the surface region with a solution, such as a skin protecting barrier solution, a cleaning solution or a medicated solution. In one aspect, the spray canister device can be movably insert into and out of the toilet seat assembly and is easy to operate and use. In addition, the bidet assembly further includes a spray nozzle assembly and a drying nozzle assembly, which are adapted to wash, clean and dry the region of the human body in three dimensional moments. The removable spray canister device with the removable sleeved cover element is thus easy to carry and be re-filled with new solutions.

27 Claims, 10 Drawing Sheets

Related U.S. Application Data application No. 15/588,637, filed on May 6, 2017, and a continuation-in-part of application No. 15/588,638, filed on May 6, 2017, and a continuation-in-part of application No. 15/588,640, filed on May 6, 2017, and a continuation-in-part of application No. 15/649,564, filed on Jul. 13, 2017.

(60) Provisional application No. 62/363,234, filed on Jul. 16, 2016, provisional application No. 62/363,232, filed on Jul. 16, 2016.

(51) Int. Cl.

| | | |
|---|---|---|
| *E03D 9/08* | (2006.01) | |
| *A47K 10/48* | (2006.01) | |
| *A47K 13/24* | (2006.01) | |
| *A61M 11/00* | (2006.01) | |
| *A61M 11/08* | (2006.01) | |
| *A61M 15/00* | (2006.01) | |
| *A61M 35/00* | (2006.01) | |
| *B05B 15/70* | (2018.01) | |
| *B65D 83/14* | (2006.01) | |
| *B65D 83/26* | (2006.01) | |
| *B65D 83/38* | (2006.01) | |
| *B05B 12/00* | (2018.01) | |

(52) U.S. Cl.
CPC ............ *A61M 3/0279* (2013.01); *A61M 3/06* (2013.01); *A61M 11/08* (2013.01); *B05B 12/002* (2013.01); *B65D 83/759* (2013.01); *E03D 9/08* (2013.01); *A61M 15/009* (2013.01); *A61M 2205/3561* (2013.01); *A61M 2205/505* (2013.01); *B05B 15/70* (2018.02); *B65D 83/267* (2013.01); *B65D 83/386* (2013.01)

(58) Field of Classification Search
USPC ...................................................... 4/447–448
See application file for complete search history.

(56) References Cited

U.S. PATENT DOCUMENTS

| | | | |
|---|---|---|---|
| 3,306,252 | A | 2/1967 | Knight |
| 3,516,424 | A | 6/1970 | Eagle |
| 3,810,260 | A | 5/1974 | Lodi |
| 3,995,326 | A | 12/1976 | Umann |
| 4,279,362 | A | 7/1981 | Pursell |
| 4,287,618 | A | 9/1981 | Silver |
| 4,327,560 | A | 5/1982 | Leon et al. |
| D266,758 | S | 11/1982 | Johannsen |
| 4,422,189 | A | 12/1983 | Couvrette |
| D279,184 | S | 6/1985 | Sakamoto |
| 4,628,548 | A | 12/1986 | Kurosawa et al. |
| D303,966 | S | 10/1989 | Fritzsche |
| 4,903,347 | A | 2/1990 | Garcia et al. |
| 4,987,617 | A | 1/1991 | Furukawa et al. |
| 5,031,252 | A | 7/1991 | Oyama |
| 5,101,520 | A | 4/1992 | Lockhart |
| 5,201,080 | A | 4/1993 | Tanaka et al. |
| 5,203,037 | A | 4/1993 | Kang |
| 5,247,711 | A | 9/1993 | Kwon |
| 5,335,855 | A | 8/1994 | Borod |
| D355,246 | S | 2/1995 | Kawamura |
| 5,409,167 | A | 4/1995 | Borod |
| D367,922 | S | 3/1996 | Kobayashi |
| 5,504,948 | A | 4/1996 | Chandler |
| 5,551,098 | A | 9/1996 | Wilk |
| 5,566,402 | A | 10/1996 | Agha el.Rifai et al. |
| 5,630,234 | A | 5/1997 | Childs |
| D387,851 | S | 12/1997 | Pieters |
| 5,720,054 | A | 2/1998 | Nakayama et al. |
| 5,765,238 | A | 6/1998 | Furukawa et al. |
| 5,813,060 | A | 9/1998 | Klopocinski |
| 5,864,894 | A | 2/1999 | Fedele |
| 5,898,956 | A | 5/1999 | Kurisaki et al. |
| 5,911,516 | A | 6/1999 | Chang |
| 5,953,765 | A | 9/1999 | Hayashi et al. |
| 5,987,659 | A | 11/1999 | Cannizzaro |
| 6,003,159 | A | 12/1999 | Sadegh et al. |
| 6,009,570 | A | 1/2000 | Hargest |
| D423,655 | S | 4/2000 | Otte |
| 6,073,275 | A | 6/2000 | Klopocinski |
| 6,105,178 | A | 8/2000 | Kurisaki et al. |
| D432,220 | S | 10/2000 | Hulsebus |
| 6,128,788 | A | 10/2000 | Yamazaki |
| D435,638 | S | 12/2000 | Merry |
| 6,167,577 | B1 | 1/2001 | Hammad |
| 6,178,568 | B1 | 1/2001 | Boulieris |
| 6,192,527 | B1 | 2/2001 | Paul |
| D451,076 | S | 11/2001 | Sommer et al. |
| D451,177 | S | 11/2001 | Scholpp |
| 6,339,852 | B1 | 1/2002 | Huang |
| 6,397,406 | B1 | 6/2002 | Moshkovich |
| 6,449,780 | B1 | 9/2002 | Merry |
| 6,481,590 | B1 | 11/2002 | Simkins |
| D471,966 | S | 3/2003 | Takahashi |
| D481,016 | S | 10/2003 | Hillis |
| D485,337 | S | 1/2004 | Tani |
| 6,688,500 | B1 | 2/2004 | Cheng |
| 6,691,328 | B2 | 2/2004 | Delfino |
| 6,754,912 | B1 | 6/2004 | Hayashi et al. |
| D500,130 | S | 12/2004 | Jung |
| D508,733 | S | 8/2005 | Peng |
| D512,425 | S | 12/2005 | Nakagawa |
| 6,973,679 | B1 | 12/2005 | Schad |
| 7,096,518 | B2 | 8/2006 | Takenaga |
| D528,991 | S | 9/2006 | Katsuyama et al. |
| 7,120,946 | B1 | 10/2006 | Lazar |
| 7,127,750 | B2 | 10/2006 | Lim |
| D533,788 | S | 12/2006 | Kleiman |
| 7,155,755 | B2 | 1/2007 | Olivier |
| D538,907 | S | 3/2007 | Kaule |
| 7,191,473 | B2 | 3/2007 | Matsomoto et al. |
| D541,225 | S | 4/2007 | Katsuyama et al. |
| 7,216,374 | B2 | 5/2007 | Hassan |
| 7,284,285 | B2 | 10/2007 | Scalzi |
| 7,287,286 | B2 | 10/2007 | Lee |
| D554,613 | S | 11/2007 | Nakatani |
| D558,181 | S | 12/2007 | Takada |
| D564,976 | S | 3/2008 | Billings et al. |
| D565,554 | S | 4/2008 | Fan |
| D578,515 | S | 10/2008 | Ikeda et al. |
| D579,342 | S | 10/2008 | Priestman |
| D583,030 | S | 12/2008 | Kobayashi |
| D594,537 | S | 6/2009 | Driedger |
| D594,945 | S | 6/2009 | Nakasaki et al. |
| 7,543,339 | B1 | 6/2009 | Harris |
| D608,426 | S | 1/2010 | Watanabe |
| D616,445 | S | 5/2010 | Wong et al. |
| D634,735 | S | 3/2011 | Maier |
| D639,399 | S | 6/2011 | Takeuchi |
| D639,400 | S | 6/2011 | Kang |
| 7,954,181 | B2 | 6/2011 | Lim |
| 8,060,953 | B1 | 11/2011 | Dorra |
| D654,808 | S | 2/2012 | Gidlow |
| 8,161,580 | B2 | 4/2012 | Hashidume et al. |
| 8,261,377 | B2 | 9/2012 | Oh |
| D668,642 | S | 10/2012 | Feldman et al. |
| 8,291,527 | B2 | 10/2012 | Pan et al. |
| D670,659 | S | 11/2012 | Ishikawa et al. |
| D671,935 | S | 12/2012 | Mao |
| 8,365,317 | B1 | 2/2013 | Dorra |
| 8,425,475 | B2 | 4/2013 | Sodo |
| D682,246 | S | 5/2013 | Boqueho |
| D688,359 | S | 8/2013 | Ogata et al. |
| D692,417 | S | 10/2013 | Tu |
| D692,541 | S | 10/2013 | Hosoi et al. |
| D698,754 | S | 2/2014 | Vignau-Lous |
| D703,797 | S | 4/2014 | Shinozaki |
| D704,316 | S | 5/2014 | Yoshioka |

(56) References Cited

U.S. PATENT DOCUMENTS

| | | |
|---|---|---|
| D704,317 S | 5/2014 | Ando |
| D706,402 S | 6/2014 | Yeung |
| D708,954 S | 7/2014 | Barnes |
| 8,776,278 B1 | 7/2014 | Dorra |
| D713,815 S | 9/2014 | Ookawa |
| D715,774 S | 10/2014 | Lee et al. |
| D716,768 S | 11/2014 | Kim |
| D717,930 S | 11/2014 | Kergoet |
| 8,904,575 B1 | 12/2014 | Lindheimer et al. |
| D724,058 S | 3/2015 | Chandel |
| D724,059 S | 3/2015 | Kim |
| 9,049,970 B2 | 6/2015 | Dorra |
| D750,765 S | 3/2016 | Giametta |
| 9,273,454 B2 | 3/2016 | Slawinski |
| 9,279,241 B2 | 3/2016 | Morioka et al. |
| D753,095 S | 4/2016 | Moran |
| 9,464,425 B2 | 10/2016 | Bailey |
| D781,808 S | 3/2017 | Pista |
| D792,867 S | 7/2017 | Murphy |
| D805,615 S | 12/2017 | Peng |
| 9,889,982 B2 | 2/2018 | Falcon |
| 2003/0140407 A1 | 7/2003 | Matsumoto et al. |
| 2004/0055080 A1 | 3/2004 | Marshall |
| 2005/0000006 A1 | 1/2005 | Takenaga |
| 2005/0010997 A1 | 1/2005 | Olivier |
| 2006/0000012 A1 | 1/2006 | Schad |
| 2006/0265801 A1 | 11/2006 | Riccobon |
| 2007/0241929 A1 | 10/2007 | Marchetto |
| 2008/0047055 A1 | 2/2008 | Lim |
| 2008/0055394 A1 | 3/2008 | Shiue |
| 2008/0201837 A1 | 8/2008 | Oh |
| 2008/0251551 A1 | 10/2008 | Huber |
| 2009/0313752 A1 | 12/2009 | Kunimoto et al. |
| 2010/0012685 A1 | 1/2010 | Ramsey |
| 2010/0152475 A1 | 6/2010 | Raichle |
| 2010/0176224 A1 | 7/2010 | Hasselschwert |
| 2011/0132929 A1 | 6/2011 | Bennett |
| 2011/0133001 A1 | 6/2011 | Cooper |
| 2011/0191950 A1 | 8/2011 | Liu |
| 2011/0203044 A1 | 8/2011 | Lim |
| 2012/0005817 A1 | 1/2012 | Jeong |
| 2012/0011647 A1 | 1/2012 | Mochita |
| 2012/0150148 A1 | 6/2012 | Shi |
| 2012/0180785 A1 | 7/2012 | Trill |
| 2012/0266483 A1 | 10/2012 | Palermo et al. |
| 2013/0133131 A1 | 5/2013 | Peng |
| 2013/0180041 A1 | 7/2013 | Ding |
| 2013/0267890 A1 | 10/2013 | Li |
| 2014/0042195 A1 | 2/2014 | Geis |
| 2014/0047626 A1 | 2/2014 | Dorra |
| 2014/0068862 A1 | 3/2014 | Al-Jafar |
| 2014/0101838 A1 | 4/2014 | Gupta et al. |
| 2014/0107409 A1 | 4/2014 | Bailey et al. |
| 2015/0000025 A1 | 1/2015 | Clements |
| 2015/0059076 A1 | 3/2015 | Tiagai |
| 2015/0203279 A1 | 7/2015 | Falcon |
| 2015/0225167 A1 | 8/2015 | Andersen |
| 2015/0337525 A1 | 11/2015 | Bailey |
| 2016/0316978 A1 | 11/2016 | Peng |
| 2017/0021116 A1 | 1/2017 | Rahmel |
| 2017/0142306 A1 | 5/2017 | Peng |
| 2017/0265624 A1 | 9/2017 | Wilson |
| 2017/0319794 A1 | 11/2017 | Schwab |
| 2017/0321406 A1 | 11/2017 | Schwab |
| 2017/0321407 A1 | 11/2017 | Schwab |
| 2017/0321408 A1 | 11/2017 | Schwab |
| 2018/0015238 A1 | 1/2018 | Schwab |
| 2018/0036473 A1 | 2/2018 | Schwab |
| 2018/0044903 A1 | 2/2018 | Schwab |

FOREIGN PATENT DOCUMENTS

| | | |
|---|---|---|
| DE | 1625201 | 2/1970 |
| EM | 025022450001 | 7/2014 |
| EP | 2138640 | 12/2009 |
| FR | 2671294 | 7/1992 |
| FR | 2869596 | 11/2005 |
| GB | 2351779 | 1/2001 |
| IN | 2689190001 | 10/2015 |
| JP | S4815806 | 2/1973 |
| JP | H0893034 | 4/1996 |
| JP | H0988165 | 3/1997 |
| JP | H1163666 | 3/1999 |
| JP | 2001279778 | 10/2001 |
| JP | 2003286738 | 10/2003 |
| JP | 2003342993 | 12/2003 |
| JP | 2007321443 | 12/2007 |
| JP | 2015206183 | 11/2015 |
| TW | 469317 | 12/2001 |
| WO | WO 2008/024005 A2 | 2/2008 |
| WO | 2013020240 | 2/2013 |
| WO | WO 2012/044086 A2 | 4/2017 |

OTHER PUBLICATIONS

PCT Notification of Transmittal of The International Search Report and The Written Opinion of The International Searching Authority, or Declaration, PCT/US2017/031482, filed on May 6, 2017 by Whole Bath, LLC.

PCT Notification of Transmittal of The International Search Report and The Written Opinion of The International Searching Authority, or Declaration, PCT/US2017/031483, filed on May 6, 2017 by Whole Bath, LLC.

PCT Notification of Transmittal of The International Search Report and The Written Opinion of The International Searching Authority, or Declaration; PCT/US2017/031484, filed on May 6, 2017 by Whole Bath, LLC.

U.S. Appl. No. 15/649,564, filed Jul. 13, 2017, entitled "Spray Canister Device with Removable Sleeved Cover."

U.S. Appl. No. 15/588,635, filed May 6, 2017, entitled "Seat and Cover System with Dynamic Spray Nozzle."

U.S. Appl. No. 15/588,637, filed May 6, 2017, entitled "Dynamic Drying Mechanism for a Wash and Clean System."

U.S. Appl. No. 15/588,638, filed May 6, 2017, entitled "Seat and Cover System with Medical Units."

U.S. Appl. No. 15/588,640, filed May 6, 2017, entitled "Medicine Delivery, Wash, Clean and Air Dry System."

U.S. Appl. No. 15/230,143, filed Aug. 5, 2016, entitled "Remote-Controlled Medicine Delivery System."

U.S. Appl. No. 15/674,536, filed Aug. 11, 2017, entitled "Method and a Wash System with a Built-In Cleanser Assembly."

U.S. Appl. No. 15/847,594, filing date presently unavailable to undersigned attorney, entitled "A Wash and Clean Apparatus."

PCT Notification of Transmittal of The International Search Report and The Written Opinion of the International Searching Authority, PCT/2017/031484, dated Aug. 14, 2017.

PCT Notification of Transmittal of The International Search Report and The Written Opinion of The International Searching Authority, PCT/US2016/45932, dated Oct. 24, 2016.

PCT Notification of Transmittal of The International Search Report and The Written Opinion of The International Searching Authority, PCT/US2017/042288, dated Sep. 28, 2017.

PCT Notification of Transmittal of The International Search Report and The Written Opinion of The International Searching Authority, PCT/US2017/42253, dated Nov. 21, 2017.

U.S. Appl. No. 15/847,594, dated Dec. 19, 2019, Brian Schwab.

Final Office Action for U.S. Appl. No. 15/588,640 dated Dec. 3, 2018.

Schwabcare website 2017, http://schwabcare.com/, site visited Jan. 21, 2018.

Kohler, Self-Cleaning Wand, https://www.youtube.com/watch?v=z629hpdnWj8, published Oct. 12, 2016.

Extended European Search Report for European Application No. 17831614 dated Mar. 18, 2020.

Extended European Search Report for European Application No. 17831608.9 dated Feb. 25, 2020.

Office Action from Chinese Patent Application No. 2017800570280, with English translation, dated Nov. 27, 2019; 22 pages.

WASH, CLEAN AND DRY SYSTEM WITH REMOVABLE SPRAY CANISTER DEVICE

CROSS-REFERENCE TO RELATED APPLICATIONS

This patent application claims benefit of U.S. provisional patent application Ser. No. 62/363,232, filed on Jul. 16, 2016, and U.S. provisional patent application Ser. No. 62/363,234, filed on Jul. 16, 2016. This patent application is a continuation-in-part (CIP) of co-pending U.S. patent application Ser. No. 15/649,564, filed Jul. 13, 2017; a continuation-in-part (CIP) of co-pending U.S. patent application Ser. No. 15/588,635, filed May 6, 2017; a continuation-in-part (CIP) of co-pending U.S. patent application Ser. No. 15/588,637, filed May 6, 2017; a continuation-in-part (CIP) of co-pending U.S. patent application Ser. No. 15/588,638, filed May 6, 2017; and a continuation-in-part (CIP) of co-pending U.S. patent application Ser. No. 15/588,640, filed May 6, 2017. The disclosures of all of the above referenced US patent applications are hereby incorporated by reference.

BACKGROUND OF THE INVENTION

Embodiments of the present invention generally relate to a spray device and particularly to a spray canister device for the delivery of water, medication, solutions and/or a pharmaceutical formulation to a surface area of a human subject using a bidet or other modern toilet seat system. More specifically, aspects of the present invention provide a method and device for delivering and applying water, medication, and/or a cleaning solution to a region of a human body (e.g., genital or anal area, intimate parts, perineal region) and cleaning thereof.

DESCRIPTION OF THE RELATED ART

Bidets and other modern toilet seat systems have been used to spray water and clean private parts of a user using a toilet. The bidet systems are used for washing the genital and anal areas using cleaning water of appropriate temperature sprayed from the center of the bidet system, instead of a toilet paper after relief stool or urination. Originally being developed for washing the pubic area of females, bidet systems are now popular among people of all ages and both sexes because it is known to be more hygienic to wash the intimate parts and anus with water instead of paper after relief. In addition, cleansing the pubic/ anal regions with water may help to avoid infection and prevent hemorrhoids and other anal disease. Furthermore, it is very effective for women with gynecological diseases. It is also very useful for the elderly or obese people to relieve themselves with great convenience.

People who have problems controlling their urine or bowels and suffer from incontinence are at risk of skin problems around the buttocks, hips, genitals, and the area between the pelvis and rectum (perineum). Excess moisture in these areas may result in skin problems (e.g., redness, peeling, irritation, and yeast infections, etc.), and if the person spends most of his or her day in a wheelchair, or bed, it is likely that bedsores may also develop. Such skin problem may be worse if the person uses diapers and other products, which allow urine or stool to be in constant contact with the skin. As such, special care by cleaning and drying the area right away after urinating or having a bowel movement, and/or cleaning the skin with mild, dilute soap and water then rinsing well and gently patting dry.

In addition, moisturizing creams can help keep the skin moist. Also, a skin sealant or moisture barrier, barrier creams or ointments that contain occlusive, barrier-type topical, such as zinc oxide, lanolin, or petrolatum can form a protective barrier on the skin. Some skin care products, often in the form of a spray or a towelette, create a clear, protective film over the skin. A doctor or nurse can recommend barrier creams to help protect the skin. There are a wide variety of ointments, creams or lotions known and available in the market for the treatment of diaper rash or incontinence. Most of these products include ingredients that offer some beneficial property to the product, for example, by acting as a water repellant, emollient, neutralizer or antibiotic. Examples of ingredients that are commonly included in such ointments are mineral oil, silicone fluids (e.g., dimethicone and cyclomethicone), petrolatum, cod liver oil, lanolin, zinc oxide, talc, calamine, kaolin, topical starch and allantoin. For example, Desitin® ointment (Pfizer, Inc.) is probably the most common topical used in treating diaper rash. It contains common barrier materials (zinc oxide and petrolatum) and additionally contains two common skin conditioning agents (cod liver oil and lanolin).

If the individual is alone, applying skin protection paste, ointments, barrier sprays, lotions, solutions, and fluids to an individual's skin is impossible since an individual cannot adequately apply skin protection fluid onto hard-to-reach areas of his or her own back and bottom. Accordingly, it is necessary to utilize the services of a second individual to apply the skin protection fluid on hard-to-reach areas such as the back and upper neck. Thus, there is a need for using a spray device, which applies barrier materials, medicated solutions, fluids, protectants, suspensions, or paste to the skin area of a person, to be incorporated into a bidet seat cleaning system having a water spray nozzle for washing and cleaning private parts of the person.

SUMMARY OF THE INVENTION

The present invention generally provides a method and a wash, dry, clean, and protect system that is easy to handle for washing, drying, and the delivery of water, medication, cleaning solutions, moisturizing creams, skin sealant, moisture barrier, medicaments, and/or a pharmaceutical formulation to a surface area of a human subject. In one embodiment, a wash and dry system is provided and includes a toilet seat assembly, a spray canister device inside a housing of the toilet seat assembly, and a wash nozzle assembly inside the housing of the toilet seat assembly. In another embodiment, the wash and dry system further includes a medicine delivery assembly.

In one aspect, the wash and dry system further includes a dryer assembly. In another aspect, the dryer assembly is able to move back and forth, sideway, and/or rotatably in a three-dimensional direction. In addition, the spray nozzle assembly is able to move back and forth, sideway, and/or rotatably in three-dimensional direction.

In still another aspect, the spray nozzle assembly and the dryer assembly can be combined and formed into a dynamic dryer and spray nozzle assembly. Further, the dynamic dryer and spray nozzle assembly is able to move back and forth, sideway, and/or rotataly in three-dimensional direction.

In another embodiment, the spray canister device of the wash and dry system may include a sleeved cover element and a canister element. In one example, the spray canister device is removable and can be installed in and out of the housing of the wash and dry system through a cover on the housing of the toilet seat assembly. In one aspect, the spray canister device is a stand-aloe device for spraying the barrier of material or medicament or a solution on to a surface area of a human subject. In another aspect, the sleeved cover element of the spray canister device can be separated from the canister element.

In one example, the sleeved cover element o the spray canister device comprises an opening, a sleeve, portion, and a trigger bar. In addition, the sleeve cover element may include a handle grip for easy gripping and easy handling of the spray canister device. In another example, the canister element of the spray canister device includes a top outlet, a bottom portion, and a canister body.

In still another embodiment, the interior content of the canister element is sprayed out of the spray canister device by triggering the trigger bar of the sleeved cover element against the spray canister element and moving the bottom portion of the canister element to be closer to the opening of the sleeved cover element.

Another embodiment of the invention provides a method for using a wash and dry system. The method includes positioning a wash and dry system near a surface area of a subject, where the wash and dry system includes a toilet seat assembly comprising a housing, a spray canister device inside the housing, and a spray nozzle assembly inside the housing. The method further includes washing the surface area of the subject using the spray nozzle assembly, and applying a spray delivered from an opening of the spray canister device onto the surface area of an object.

In one aspect, the method further includes, optionally, cleaning the surface area of the subject using a cleaning solution sprayed from the wash and dry system. In another aspect, the method further includes drying the surface area of the subject using a dryer assembly of the wash and dry system.

In one example, drying the surface area is performed by the dryer assembly at high power prior to applying the spray delivered from the spray canister device. In another example, drying the surface area is performed by the dryer assembly at low power after applying the spray delivered from the spray canister device.

Further, the method may also include installing the spray canister device into the housing of the toilet seat assembly prior to using the wash and dry system. In one example, the spray canister device is installed by gripping a handle grip of the spray canister device and positioning the spray canister device into a cover of the housing of the toilet seat assembly. In another example, the spray canister device is installed by coupling a trigger bar of the spray canister device securely onto a delivery rack inside the housing of the toilet seat assembly.

In another embodiment, the method may further include shaking the spray canister device by moving the spray canister device inside the housing of the toilet seat assembly. In one aspect, shaking the sprat canister device is performed prior to applying the spray delivered from the spray canister device.

In still another embodiment, the method may further include applying the spray by moving a canister element of the spray canister device against a sleeved cover element of the spray canister device along a delivery rack inside the housing of the toilet seat assembly.

In one embodiment, the removable sleeved cover element of the spray canister device includes a top cap portion, an opening, a sleeve portion, a handle grip, and a trigger bar. In another embodiment, the inner canister element includes a top outlet and a canister body. In still another embodiment, the canister body of the inner canister element is covered by a sleeved portion of the removable sleeved cover element and the top outlet is fitted to channels inside the top cap portion of the removable sleeved cover.

In a further embodiment, a spray canister device is incorporated into a wash, clean and dry bidet system that is designed to easily dispense water, medication, cleaning solutions, moisturizing creams, skin sealant, moisture barrier, medicaments, and/or a pharmaceutical formulation from a wash, clean, and dry bidet system to a surface area of a human subject.

The wash and dry system of the present invention applies barrier materials, skin protection lotions and oils, medicaments directly to the skin and an operator of the wash and dry system will be able to spray lotions evenly on the individual, especially in hard-to-reach areas such as the bottom, back and neck of a human subject.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

The present invention includes a method and a wash, dry, clean, and protect system for providing easy washing, cleaning and protection of a person's bottom while using a toilet is provided. In one embodiment, the system can be placed directly over a rim of a toilet bowl or a seat of a toilet seat system. In another embodiment, the wash, dry, clean, and protect system include a removable spray canister device for the delivery of water, medication, cleaning solutions, moisturizing creams, skin sealant, moisture barrier, medicaments, and/or a pharmaceutical formulation to a surface area of a human subject.

The spray canister device as described herein is easy-to-handle and makes it easy to apply and spray fluids, solutions, suspensions, or paste of a barrier chemical or medicament to the skin area of a person. The spray canister device contains a removable sleeved cover element and a canister element to allow for easy operation and make it easy to spray, and can be handled manually or can function together with a toilet seat wash and dry system or other devices.

In one embodiment, a spray canister device is incorporated into a wash, clean and dry bidet system and is designed to easily dispense water, medication, cleaning solutions, moisturizing creams, skin sealant, moisture barrier, medicaments, and/or a pharmaceutical formulation from a wash, clean and dry bidet system to a surface area of a human subject.

Figure 1:
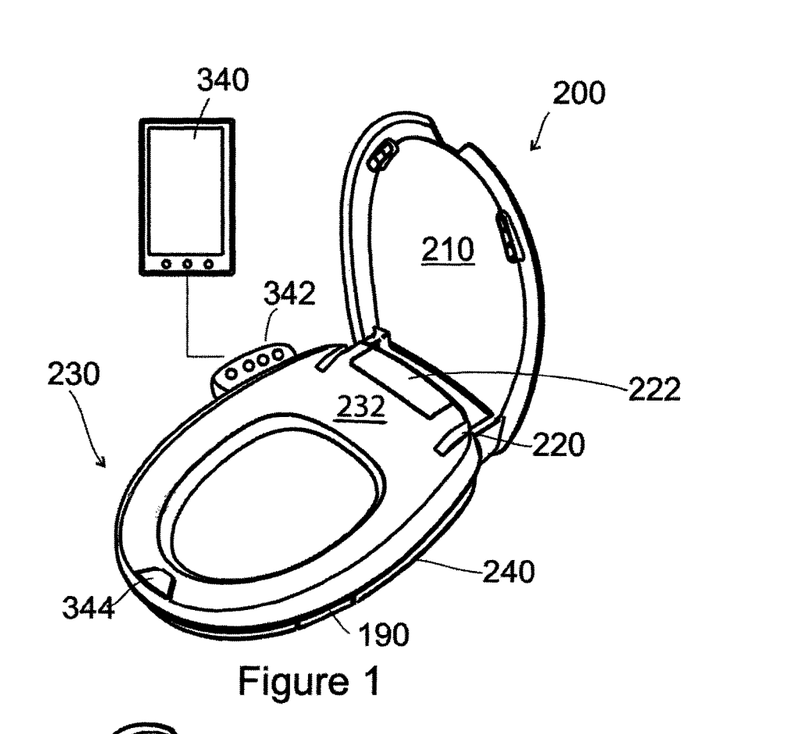
FIG. 1 is a perspective view of a wash and dry system with a spray canister device therein according to one embodiment of the invention.

FIG. 1 is a perspective view of a wash and dry system with a spray canister device 100 (shown in FIG. 2B) according to one embodiment of the invention. In one embodiment, the wash and dry system includes a toilet seat assembly 200 with the spray canister device 100 positioned stationary or removably inside a base housing 220 of the toilet seat assembly 200. In general, the toilet seat assembly 200 includes a seat cover 210, the base housing 220, a base housing cover 222, a seat 230, a seat body 232, and a base 240.

In one example, the wash and dry system further includes a dryer assembly 170 (shown in FIG. 4D) and a spray nozzle assembly 160 (shown in FIG. 4D) positioned inside the base housing 220 of the toilet seat assembly 200. The dryer assembly 170 is able to move back and forth, sideways, and/or rotatably in a three-dimensional direction In addition, the spray nozzle assembly 160 is able to move back and forth, sideway, and/or rotatably in a three-dimensional direction. In another example, the dryer assembly 170 and the spray nozzle assembly 160 are combined and formed into a dynamic dryer and spray nozzle assembly, such as a wash and dry assembly 150, as shown in FIG. 4D. In one aspect, the dynamic dryer and spray nozzle assembly is able to move back and forth, sideway, and/or rotatably in three-dimensional direction.

The wash and dry system of the present invention applies barrier materials, skin protection lotions and oils, and medicaments directly to the skin and an operator of the wash and dry system will be able to spray lotions evenly on the individual, especially in hard-to-reach areas such as the bottom, back and neck of a human subject.

In addition, the wash and dry system may further include a power switch, a power indicator for powering up the system and operating wash, clean, dry, protect, and/or other functions of the system. In one aspect, the system is connected to a power cord. In another aspect, the system is connected to a battery power pack.

Figure 2A:
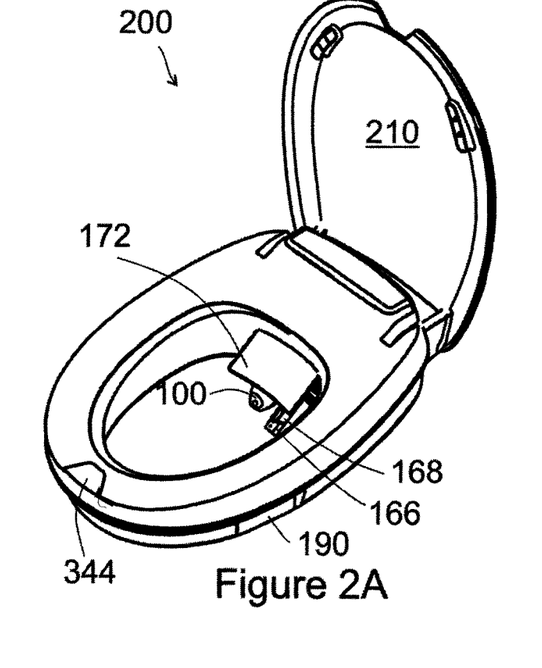
FIG. 2A is a perspective view of a wash and dry system with a spray canister device and a combined dynamic dryer and spray nozzle assembly extended out below a cover according to another embodiment of the invention.

FIG. 2A is a perspective view of one example of a wash and dry system. The wash and dry system may include the spray canister device 100 and a combined dynamic dryer and spray nozzle assembly (e.g., the wash and dry assembly 150, as shown in FIG. 4D). As shown in FIG. 2A, the spray canister device 100 and the wash and dry assembly 150 are adapted to be extended out below a cover 172, which is located near a side of the base housing 220 of the base 240.

Figure 2B:
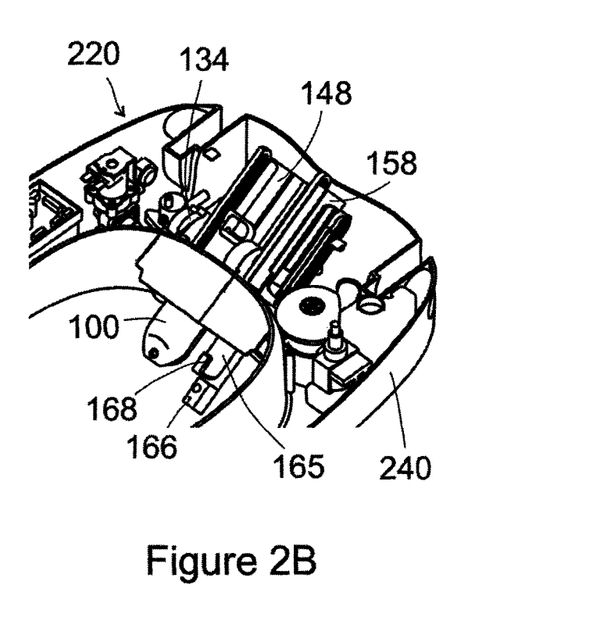
FIG. 2B is an inside view of a housing of a wash and dry system showing a spray canister device and a combined dynamic dryer and spray nozzle assembly extended from a housing of the wash and dry system and extended out below a cover of the base of the wash and dry system according to another embodiment of the invention.

FIG. 2B is an inside view of the base housing 220 of the wash and dry system having the spray canister device 100 and the wash and dry assembly 150 (shown in FIG. 4D) extended from the base housing 220 of the wash and dry system and extended out below the cover 172 of the base 240 of the wash and dry system according to another embodiment of the invention. In one embodiment, the wash and dry assembly 150 is adapted to be connected to a water inlet of a water hose assembly for supplying water and other liquid into the wash and dry system.

Figure 3:
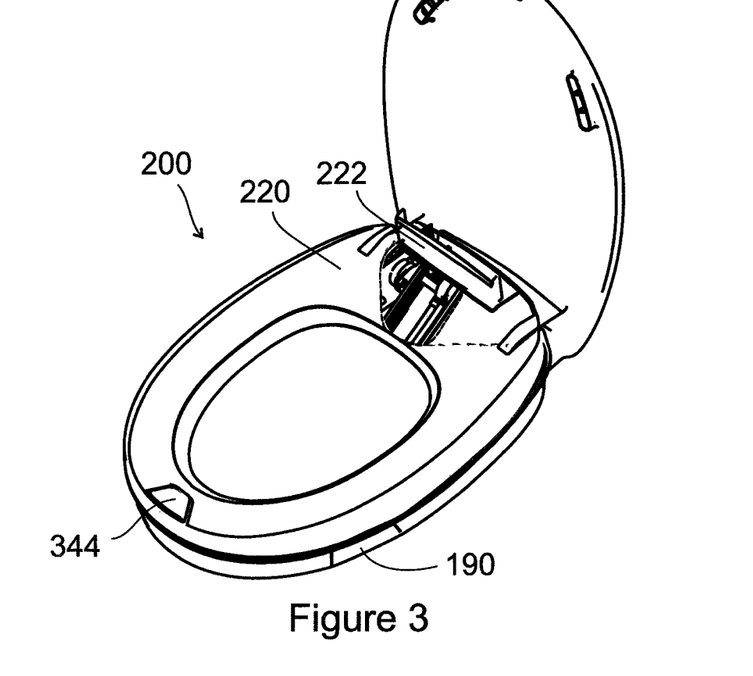
FIG. 3 is a perspective view of a wash and dry system wherein a cover positioned on a housing of a base of the wash and dry system is opened with a spray canister device stored therein according to another embodiment of the invention.

FIG. 3 is a perspective view of a wash and dry system where the base housing cover 222 positioned on the base housing 220 of the base 240 of the wash and dry system is opened with the spray canister device 100 stored therein. In one aspect, the spray canister device is adapted to be removable in and out of the base housing cover 222 of toilet seat assembly 200 of the wash and dry system.

In one embodiment, the wash and dry system further includes a medicine delivery assembly 190. The medicine delivery assembly 190 may include medication and/or cleaner solutions therein. Suitable medication and cleaning solutions are not limited and can be any of a desirable cleaning solution, a medication solution, a fragrant solution, a deodorant solution, a moisturizing solution, and/or combination thereof. In addition, the content of liquid solutions within the medicine delivery assembly 190 can be changeable according to personal preference of a user or under the instruction of a doctor for treating various perineal or urinary tract infections, vaginal infections, and/or hemorrhoids, among others.

Figure 4A:
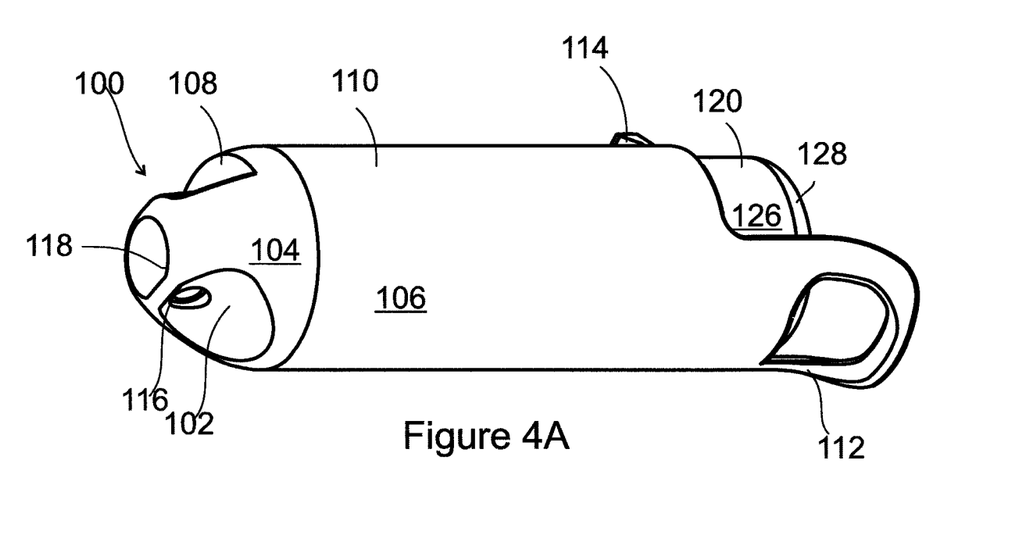
FIG. 4A is a perspective view of a spray canister device with a removable sleeved cover element and a canister element according to another embodiment of the invention.

FIG. 4A is a perspective view of the spray canister device 100. In one aspect, the spray canister device 100 includes a sleeved cover element 110 and a canister element 120 according to another embodiment of the invention. In another aspect, the sleeved cover element 110 of the spray canister device 11 can be removably separated from the canister element 120. In one example, the spray canister device 100 is a stand-alone device for spraying a barrier material or medicament or a solution on to a surface area of a human subject. In another example, the spray canister device 100 is installed into the base housing 220 of the toilet seat assembly 200 through the base housing cover 222 so as to effect spraying a barrier material or medicament or a solution on to a surface area of a human subject. In another example, the sleeved cover element 110 of the spray canister device 100 can be separated from the canister element 120.

As shown in FIG. 4A, the sleeved cover element 110 of the spray canister device 100 includes a top cap portion 104, and a sleeved portion 106. The top cap portion 104 may also include a cut-out portion 102, a top body portion 108, an opening 116, and a top flat surface portion 118. The sleeved portion 107 of the sleeved cover element 110 may also include a handle grip 112 and a trigger bar 114. The handle grip 112 of the sleeved cover element 110 is provided for easy gripping and easy handling of the spray canister device 100. In addition, the canister element 120 of the spray canister device 100 includes a top outlet, a bottom portion 128, and a canister body 126.

Figure 4B:
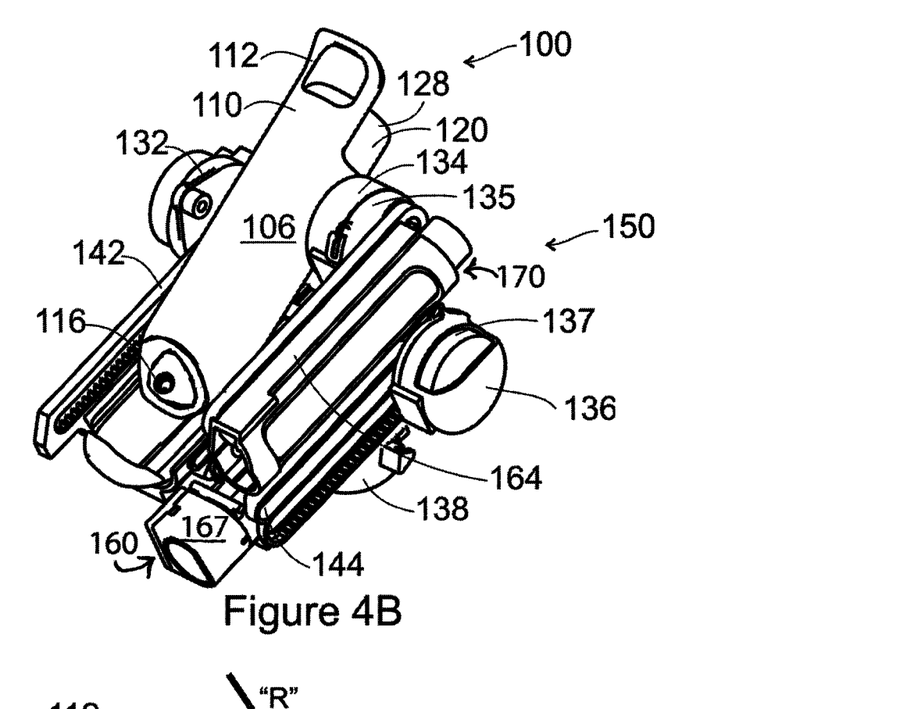
FIG. 4B is a perspective view of operating a spray canister device to fit into a delivery track positioned next to a spray nozzle assembly and a dryer assembly that are combined and formed into a dynamic dryer and spray nozzle assembly according to yet another embodiment of the invention.
Figure 4C:
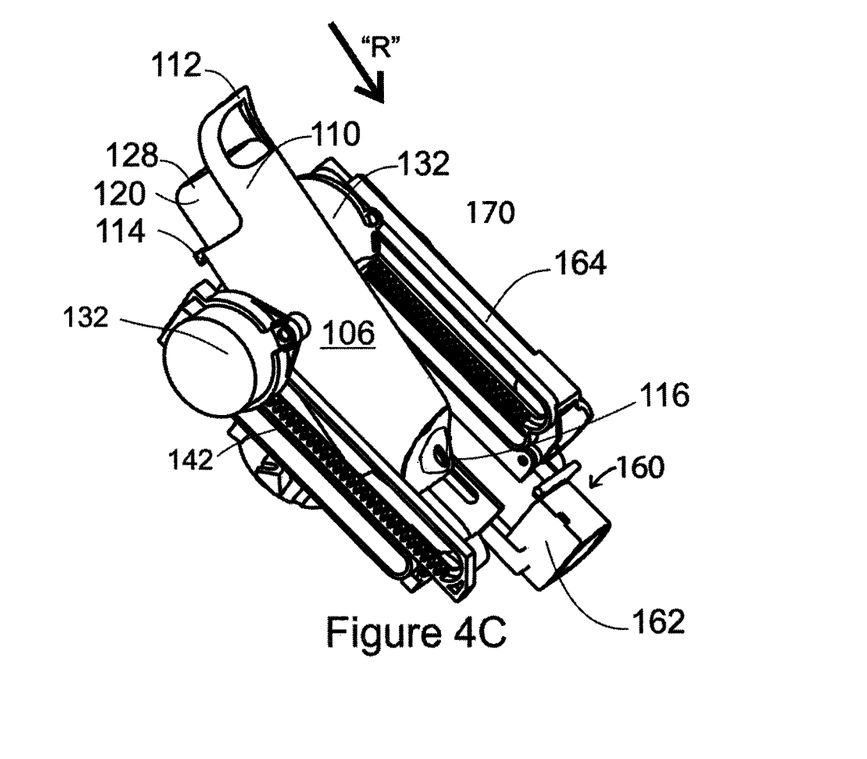
FIG. 4C is another side perspective view of installing the spray canister device of FIG. 4B to be secured onto a delivery track positioned next to a dynamic dryer and spray nozzle assembly according to yet another embodiment of the invention.
Figure 4D:
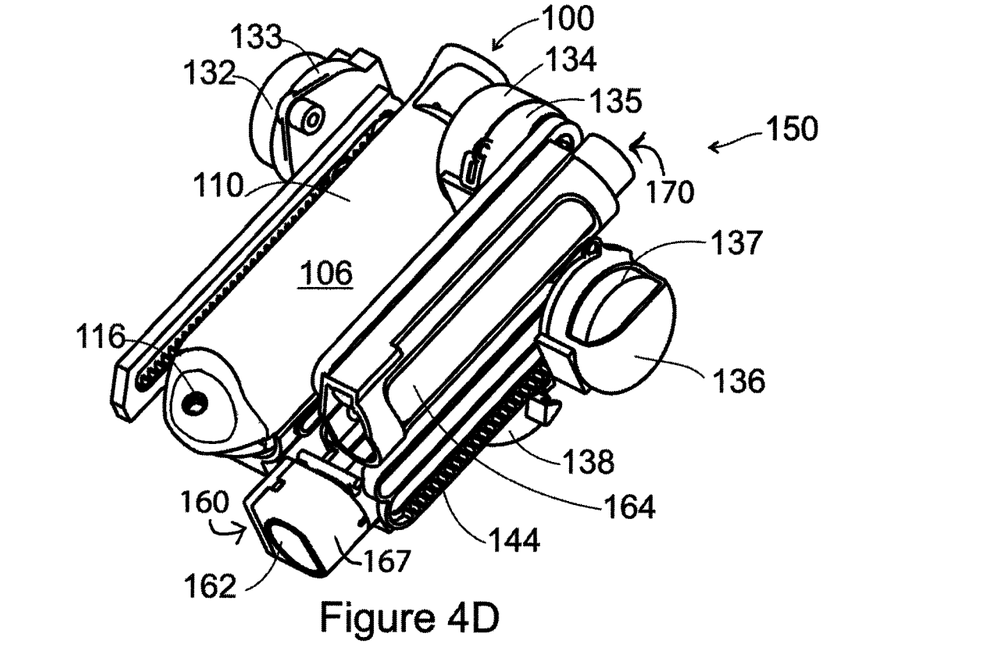
FIG. 4D is another side perspective view of the spray canister device of FIG. 4B when the spray canister device is securely installed onto a delivery track positioned next to a dynamic dryer and spray nozzle assembly according to yet another embodiment of the invention.
Figure 4E:
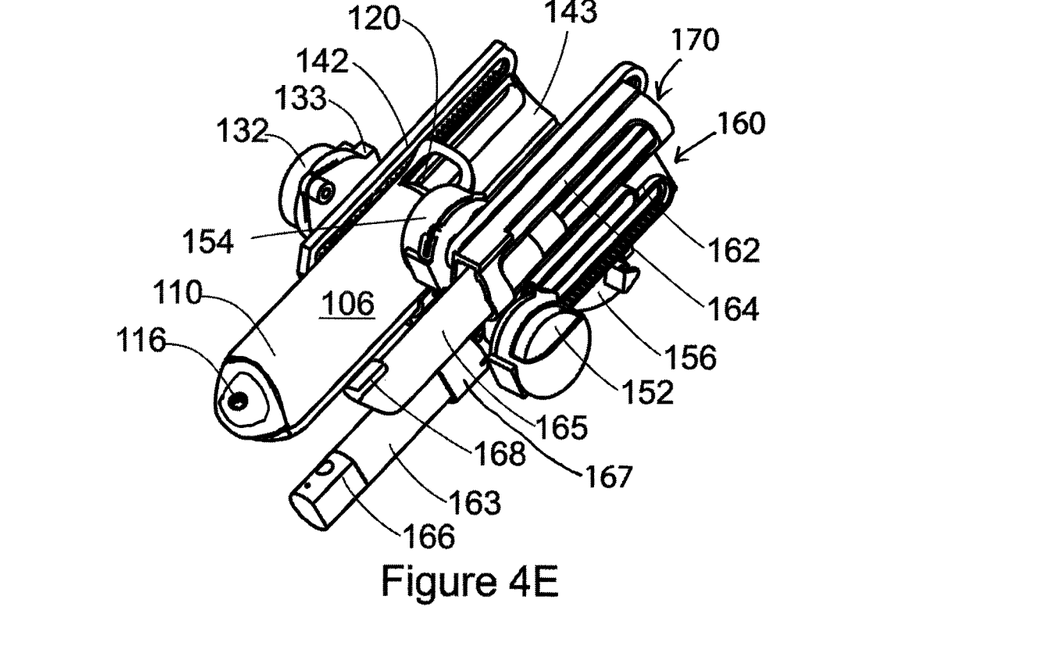
FIG. 4E is another side perspective view of the spray canister device of FIG. 4B after the spray canister device is securely installed next to a dynamic dryer and spray nozzle assembly and both the spray canister device and one or more nozzles head elements of the combined dynamic dryer and spray nozzle assembly is ready to be extended out according to yet another embodiment of the invention.

FIG. 4B is a perspective view of operating and installing the spray canister device 100 to fit into a track 143 positioned next to the wash and dry assembly 150. FIG. 4C is another side perspective view of installing the spray canister device 100 of FIG. 4B to be secured onto the track 143. FIG. 4D is another side perspective view of the spray canister device 100 of FIG. 4B when the spray canister device 100 is securely installed onto a delivery track positioned next to the wash and dry assembly 150. FIG. 4E is another side perspective view of the spray canister device of FIG. 4B after the spray canister device 100 is securely installed next to the wash and dry assembly 150 and both the spray canister device 100 and one or more nozzles head elements of the wash and dry assembly 150 is ready to be extended out.

In one embodiment, the interior content of the canister element 120 is sprayed out of the spray canister device 100 by triggering the trigger bar 114 of the sleeved cover element 110 against the canister element 120 and moving the bottom portion 128 of the canister element 120 to be closer to the opening 116 of the sleeved cover element 110.

Figure 5A:
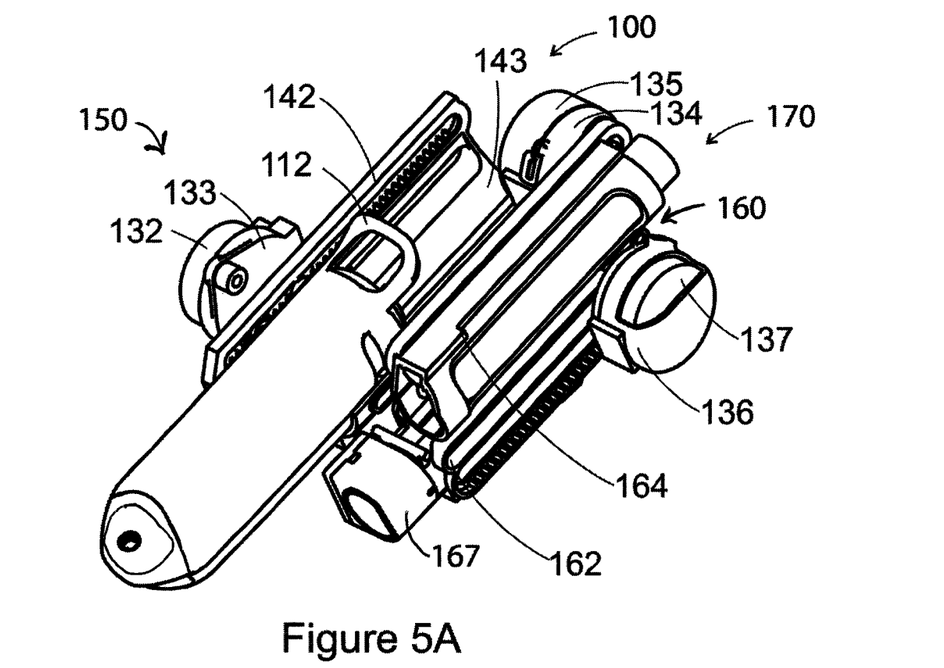
FIG. 5A is another side perspective view of the spray canister device, showing the spray canister device is being extended out and ready to spray a solution out of its front opening according to yet another embodiment of the invention.
Figure 5B:
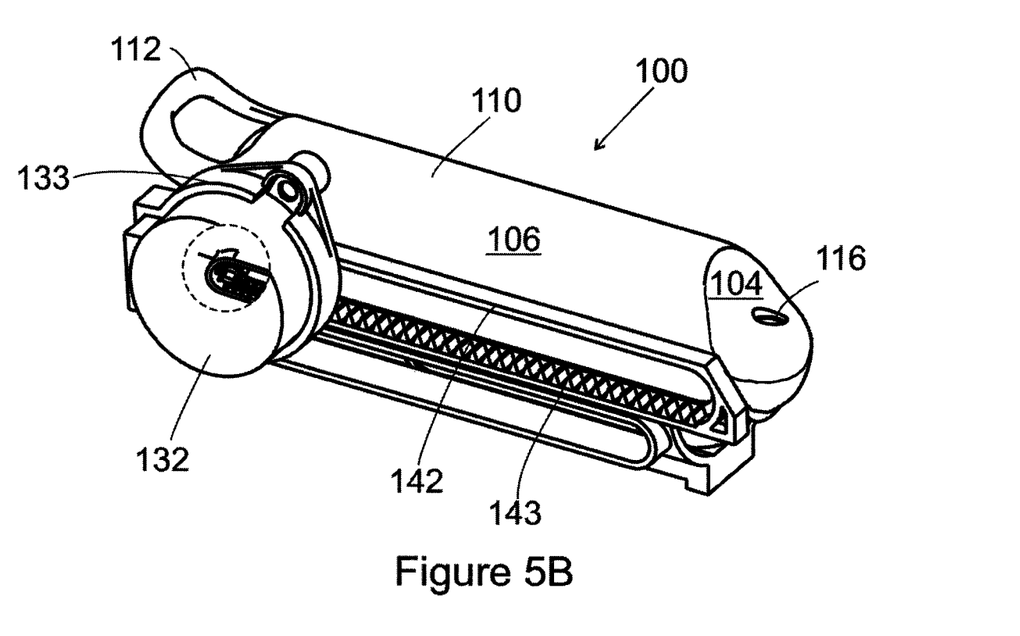
FIG. 5B is a side view of one example of a spray canister device, showing a motor, a rail, and a slot element of a driving motor assembly for moving the spray canister device according to one embodiment of the invention.

FIG. 5A is another side perspective view of the spray canister device 100, showing the spray canister device 100 is being extended out and ready to spray a solution out of the opening 116. FIG. 5B is a side view of the spray canister device 100, showing a motor 132, a motor holder 133, a track 143, and a slot element 142 of a driving motor assembly for moving the spray canister device 100.

Figure 5C:
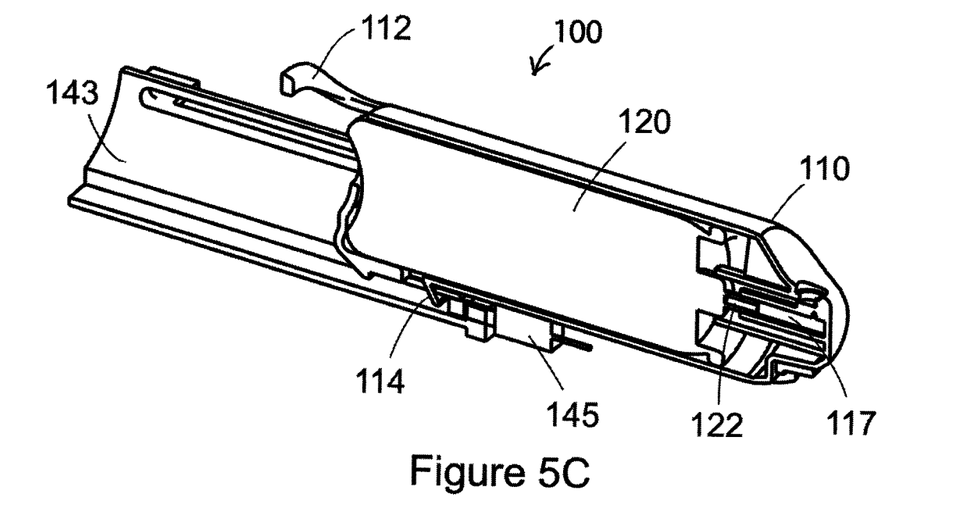
FIG. 5C is a cross-sectional view of the spray canister device of FIG. 5B, showing a driving motor assembly used to move and extend the spray canister device according to one embodiment of the invention.

FIG. 5C is a cross-sectional view of the spray canister device 100 of FIG. 5B, showing the track 143, a solenoid 145 of a driving motor assembly used to couple with the trigger bar 114 of the spray canister device 100 so as to move and extend the spray canister device 100.

Figure 6A:
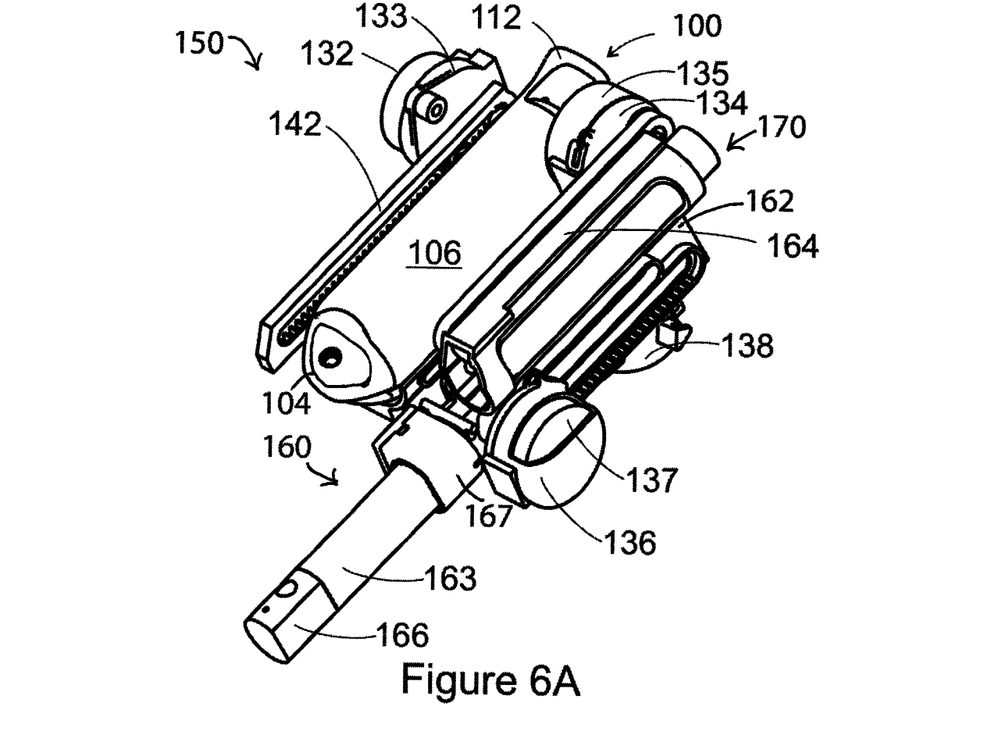
FIG. 6A is a side perspective view of a spray canister device installed next to a dynamic dryer and spray nozzle assembly, showing a spray nozzle wand of the dynamic dryer and spray nozzle assembly is being extended out of a spray nozzle housing and ready to spray water or a cleaning solution out of its front spray nozzle head according to yet another embodiment of the invention.

FIG. 6A is a side perspective view of the spray canister device 100 installed next to the wash and dry assembly 150, showing a spray nozzle wand 163 of the wash and dry assembly 150 is being extended out of a spray nozzle housing 162 and ready to spray water or a cleaning solution out of a spray nozzle head 166.

Figure 6B:
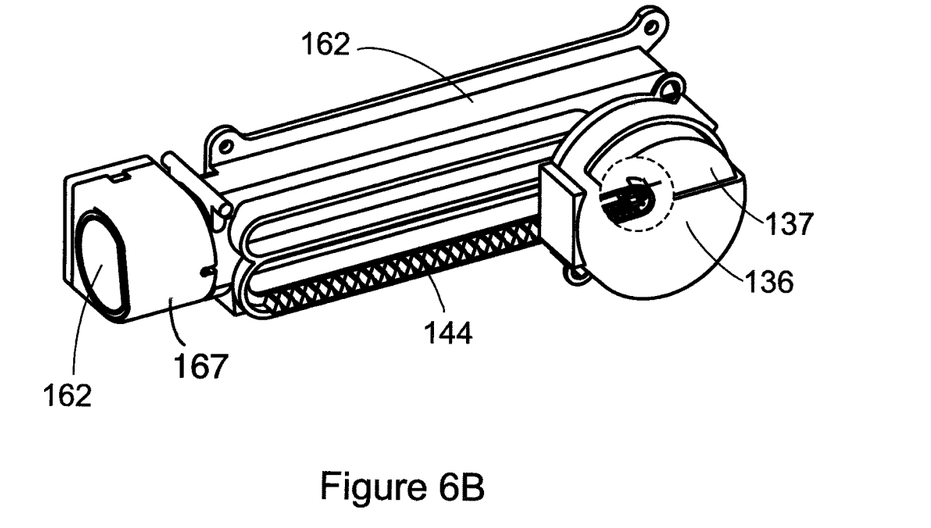
FIG. 6B is a side view of one example of a spray nozzle assembly, showing a spray nozzle housing of the spray nozzle assembly and a driving motor assembly with a motor, a rail and a slot element for moving the spray nozzle assembly according to one embodiment of the invention.

FIG. 6B is a side view of a spray nozzle assembly of the wash and dry assembly 150, showing the spray nozzle housing 162 of the spray nozzle assembly and a driving motor assembly with a motor 136, a motor holder 137, a rack 144 and a slot element for moving the spray nozzle assembly according to one embodiment of the invention.

Figure 6C:
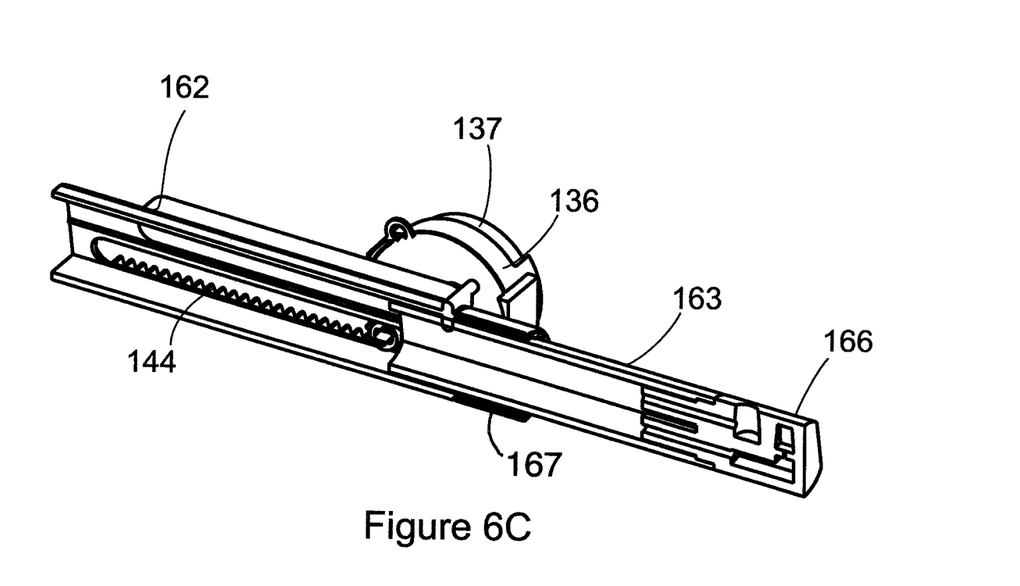
FIG. 6C is a cross-sectional view of the spray nozzle assembly of FIG. 6A, showing a drive motor assembly used to move and extend the spray nozzle assembly according to one embodiment of the invention.

FIG. 6C is a cross-sectional view of the spray nozzle assembly of FIG. 6B, showing the motor 136, the motor holder 137, and the rack 144 of the driving motor assembly used to move and extend the spray nozzle assembly.

As shown in FIG. 6A-6C, the spray nozzle assembly of the wash and dry system includes the spray nozzle wand 163 and the spray nozzle head 166 that are able to be movably extended by the motor 136 of a driving motor assembly. The spray nozzle assembly further includes one or more liquid channels therein such that the liquids flowing therein can be delivered via the spray nozzle wand 163 and the spray nozzle head 166 and sprayed out. For example, water and other liquids can be sprayed out and used to wash onto a desirable area (e.g., a genital area, an anal area, anterior private parts, perineal region, etc.) of a human body while a human is using a toilet.

The spray nozzle head of 166 is adapted to spray out liquid in a stream or a mist form onto a desirable area of a human body. The shape and size of the spray nozzle head 166 positioned at the tip of the spray nozzle wand 163 is not limited and can be a small opening, a multiple-holed nozzle type element, among others.

Suitable liquid that can be contained and flowed within the one or more channels of the spray nozzle assembly of the wash and dry assembly 150 includes water, medication solutions, cleaning solutions and combinations thereof. The temperature of about 60° C. In one embodiment, the wash and clean system includes a water inlet adapted to connect to a water hose assembly (for supplying water and other liquid into the wash and dry system. For example, the water inlet can be positioned near the back wall of the toilet seat assembly 200.

Figure 7A:
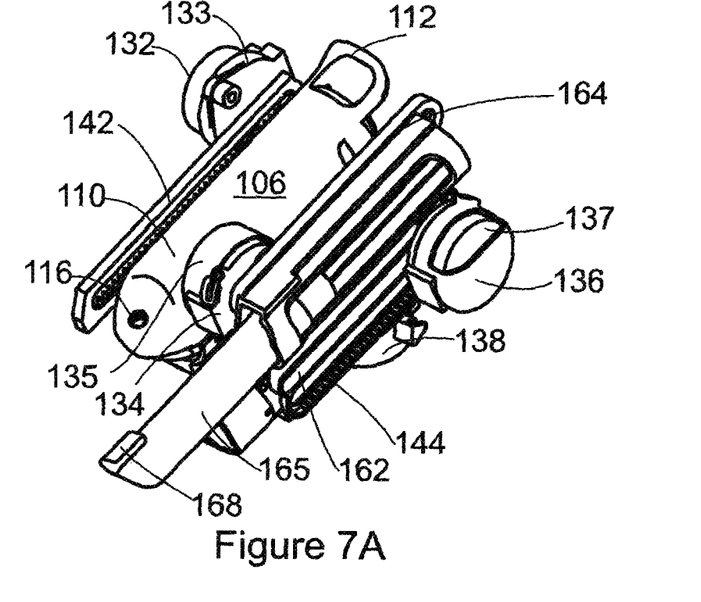
FIG. 7A is a side perspective view of a spray canister device installed next to a dynamic dryer and spray nozzle assembly, showing a dryer wand of the dynamic dryer and spray nozzle assembly extended out of a dryer housing and ready to blow air or gases out of its front blower head according to yet another embodiment of the invention.
Figure 7B:
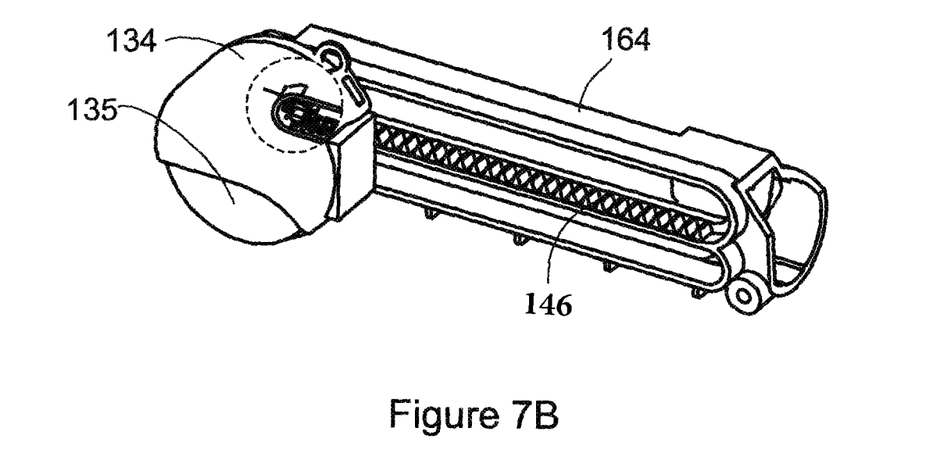
FIG. 7B is a side view of one example of a dryer assembly, showing a dryer housing of the dryer assembly according to one embodiment of the invention.
Figure 7C:
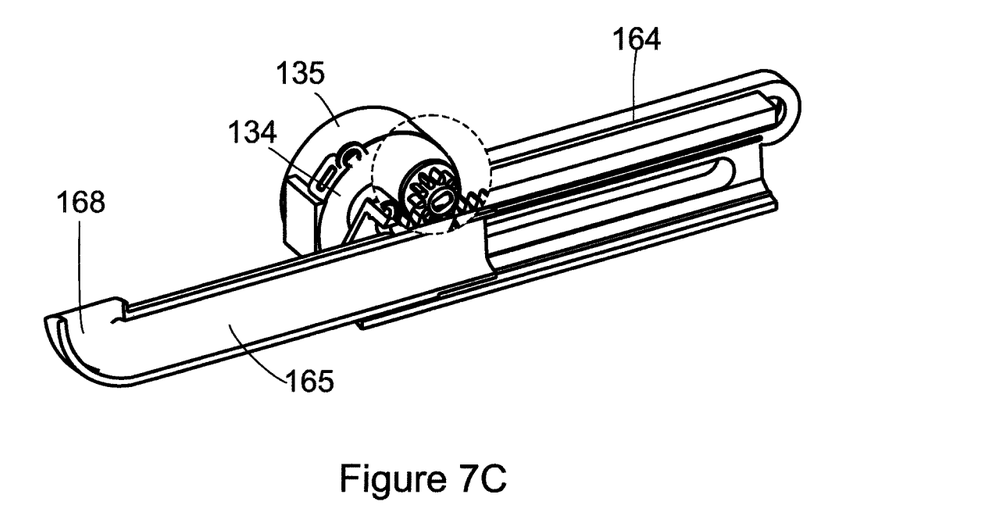
FIG. 7C is a cross-sectional view of the dryer assembly of FIG. 7A, showing a driving motor assembly used to move and extend the dryer assembly according to one embodiment of the invention.

FIG. 7A is a side perspective view of the spray canister device 100 installed next to a dynamic dryer and spray nozzle assembly, e.g., the wash and dry assembly 150 as shown, where a dryer wand 165 of a dryer assembly of the wash and dry assembly 150 is being extended out of a dryer housing 164 and ready to blow air or gases out of its front blower head. FIG. 7B is a side view of the dryer assembly, showing the dryer housing 164 of the dryer assembly and a driving motor assembly with a motor 134, a motor holder 135, a rack 146 and a slot element for moving the dryer assembly. FIG. 7C is a cross-sectional view of the dryer assembly of FIG. 7A, showing a driving motor assembly used to move and extend the dryer assembly according to one embodiment of the invention.

Referring back to FIG. 1, the wash and dry system may further includes one or more power switches or control units 340, 342, and 344 such that the various motors and electric circuits contained within the system can be turned on for powering up the system and operating wash, clean, dry, protect and other functions of the wash and dry system. The control units can be positioned, in one example, on the top or the side of the system, and can be easily visible to a user. In one embodiment, the control unit 340 is a remote control unit. In addition, one or more power indicators can be positioned on the control units 340, 342 and 344 to indicate turning on of the electric power and proper functioning of the wash and clean system. In one example, a power indicator and the control unit 344 can be positioned at or near a front side of the system as exemplarily shown in FIG. 1.

In one aspect, the wash and clean system is connected to a power cord via a power connector. The power cord is adapted to connect to an electric outlet and provide electric power to power up the wash and dry system. In another aspect, the wash and dry system is connected to a battery power pack in order to conveniently power up the wash and dry system without the need to find an electric outlet.

In operation, once the electric power is turned on and the motors within the wash and dry system are adapted to deliver all desirable liquids (e.g., water and liquid from a water hose assembly via a water inlet, a cleaning or medication liquid solution from the medicine delivery assembly 190, and combinations thereof) from one or more channels therein to the spray nozzle assembly.

Figure 8:
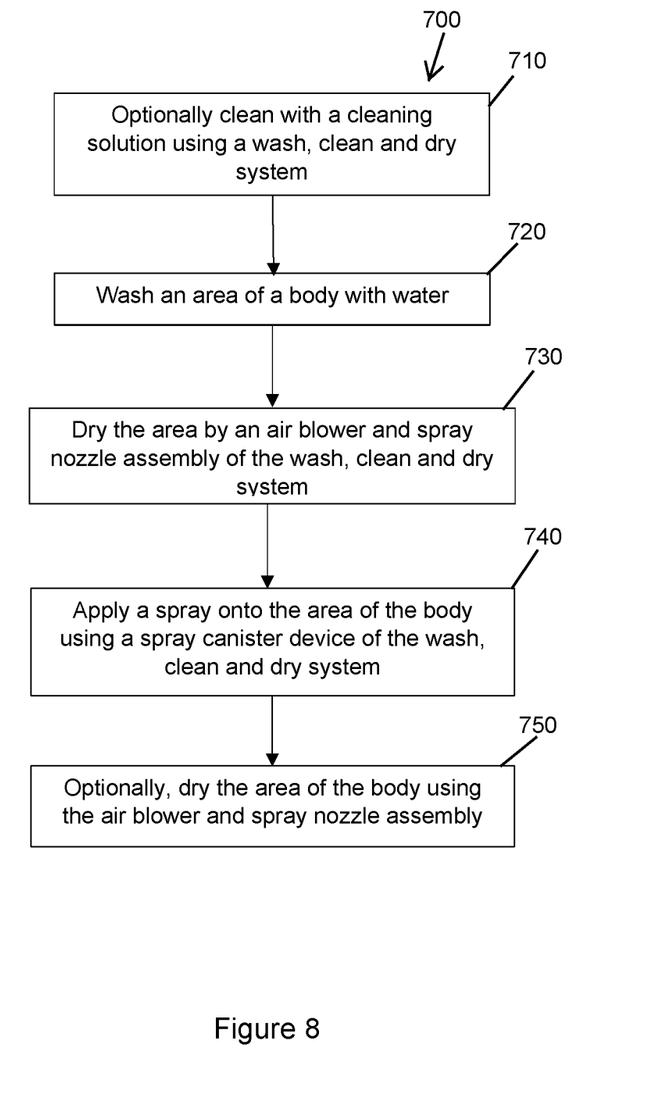
FIG. 8 illustrates a method of operating a wash and dry system with a removable spray canister device according to one or more embodiments of the invention.

FIG. 8 illustrates a method of 700 of operating a wash and dry system with a removable spray canister device according to one or more embodiments of the invention. In one aspect, the method includes, optionally, at step 710 of cleaning the surface area of the subject using a cleaning solution sprayed from the wash and dry system.

In another aspect, the method includes positioning a wash and dry system near a surface area of a subject, where the wash and dry system includes a toilet seat assembly comprising a housing, a spray canister device inside the housing, and a spray nozzle assembly inside the housing. At step 720, the surface area of the subject is washed using the spray nozzle assembly, and step 740, a spray delivered from an opening of the spray canister device is applied onto the surface area of the subject At step 730, the surface area of the subject is dried using a dryer assembly of the wash and dry system. In one example, drying the surface area is performed by the dryer assembly at high power prior to applying the spray delivered from the spray canister device. Optionally, at step 750, drying the surface area is performed by the dryer assembly at low power after applying the spray delivered from the spray canister device.

Further, the method may also include installing the spray canister device into the housing of the toilet seat assembly prior to using the wash and dry system. In one example, the spray canister device is installed by gripping a handle grip of the spray canister device and positioning the spray canister device into a cover of the housing of the toilet seat assembly. In another example, the spray canister device is installed by coupling a trigger bar of the spray canister device securely onto a delivery rack inside the housing of the toilet seat assembly.

In another embodiment, the method may further include shaking the spray canister device by moving the spray canister device inside the housing of the toilet seat assembly. In one aspect, shaking the spray canister device is performed prior to applying the spray delivered from the spray canister device.

In still another embodiment, the method may further include applying the spray by moving a canister element of the spray canister device against a sleeved cover element of the spray canister device along a delivery rack inside the housing of the toilet seat assembly.

In one embodiment, the removable sleeved cover element of the spray canister device includes a top cap portion, an opening, a sleeve portion, a handle grip, and a trigger bar. In another embodiment, the inner canister element includes a top outlet and a canister body. In still another embodiment, the canister body of the inner canister element is covered by a sleeved portion of the removable sleeved cover element and the top outlet is fitted to channels inside the top cap portion of the removable sleeved cover.

While the foregoing is directed to embodiments of the present invention, other and further embodiments of the invention may be devised without departing from the basic scope thereof, and the scope thereof is determined by the claims that follow.

The invention claimed is:

1. An apparatus for storing a first liquid product and spraying the first liquid product onto a region of the human body, comprising:
   a toilet seat assembly including a bidet seat, the bidet seat including a bidet housing; and
   a bidet assembly positioned within the bidet housing of the bidet seat;
   wherein the toilet seat assembly comprises a removable spray canister device adapted to store the first liquid product therein, the removable spray canister device configured to move between a retracted position and an extended position to selectively allow a user to spray the first liquid product onto the region of the human body.

2. The apparatus of claim 1, wherein the removable spray canister device further comprises:
   a sleeved cover element including a sleeved portion; and
   a canister element positioned within the sleeve portion of the sleeved cover element.

3. The apparatus of claim 2, wherein the sleeved cover element of the removable spray canister device further comprises:
   a trigger bar configured to facilitate relative movement between the sleeved cover element and the canister element.

4. The apparatus of claim 3, wherein the first liquid product is stored within the canister element of the removable spray canister device and the first liquid product is sprayed out of the canister element by moving the canister element and the sleeved cover element relative one another to compress an outlet of the canister element.

5. The apparatus of claim 2, wherein the sleeved cover element further comprises a handle grip adapted to facilitate insertion and removal of the removable spray canister device in an opening of the bidet housing.

6. The apparatus of claim 1, wherein the first liquid product comprises one or more of skin protectants, ointments, mineral oil, silicone fluids, dimethicone, cyclomethicone, petrolatum, cod liver oil, lanolin, zinc oxide, talc, calamine, kaolin, topical starch, allantoin, barrier materials, skin moisturizers, skin lotions, moisturizing creams, skin sealants, water, medication, cleaning solutions, moisture barriers, medicaments, a pharmaceutical formulation, and combinations thereof.

7. The apparatus of claim 1, further comprising a spray nozzle assembly, the spray nozzle assembly comprising:
a spray nozzle housing including a spray nozzle unit, the spray nozzle unit comprising a retractable spray nozzle wand that is configured to deliver a second liquid product to the region; and
at least one driving motor operatively connected to the spray nozzle wand, the at least one driving motor adapted for moving the spray nozzle wand between a retracted position and an extended position.

8. The apparatus of claim 7, wherein the at least one driving motor is further configured to rotate the spray nozzle wand of the spray nozzle unit.

9. The apparatus of claim 7, wherein the spray nozzle unit of the spray nozzle assembly further comprise:
a first spray nozzle channel configured to deliver the second liquid product to the region; and
a second spray nozzle channel configured to deliver a third liquid product to the region;
wherein the second liquid product comprises one or more of water, a cleaning solution, a barrier spray solution, a medicine-containing solution, and combinations thereof; and
wherein the third liquid product comprises one or more of water, a cleaning solution, a barrier spray solution, a medicine-containing solution, and combinations thereof.

10. The apparatus of claim 1, further comprising a drying nozzle assembly, the drying nozzle assembly comprising:
a drying nozzle unit comprising a retractable air blower wand, the retractable air blower wand adapted to deliver air at a predetermined temperature to the region of the human body; and
a fan connected to the drying nozzle unit.

11. The apparatus of claim 10, wherein the drying nozzle assembly further comprises:
at least one driving motor connected to the drying nozzle unit, the at least one driving motor adapted for moving the retractable air blower wand between a retracted position and an extended position and rotating the retractable air blower wand.

12. The apparatus of claim 1, further comprising a medicine delivery assembly having one or more medicine storage cartridges, wherein the medicine delivery assembly is adapted to deliver one or more medicine-containing products stored within the one or more medicine storage cartridges.

13. The apparatus of claim 12, further comprising a spray nozzle assembly including a spray nozzle wand, wherein the medicine delivery assembly is coupled to the spray nozzle wand.

14. The apparatus of claim 1, further comprising:
one or more control units adapted to receive a user input and, based on the user input, to extend the bidet assembly out of the bidet housing and retract the bidet assembly inside the bidet housing;
wherein the one or more control units comprises one or more of a remote control unit, a touch screen control unit, a joystick control unit, a hand-held control unit, a steering-wheel control unit, a built-in control unit adjacent the toilet seat assembly, a front end touch control unit, and combinations thereof.

15. The apparatus of claim 14, wherein one of the one or more control units is a front end touch control unit positioned at a front end of the seat body to control movement of the bidet assembly.

16. The apparatus of claim 15, wherein the front end touch control unit is a single button with electric circuits therein, and wherein the user input comprises repeated touching of the single button.

17. A method comprising:
washing, by a spray nozzle assembly of a toilet seat assembly, a perianal region of a human body with a first liquid product;
drying, by a drying nozzle assembly of the toilet seat assembly, the perianal region of the human body; and
spraying, by a removable spray canister device of the toilet seat assembly, a second liquid product on the perianal region of the human body.

18. The method of claim 17, further comprising the step of drying the region using the drying nozzle assembly when the second liquid product is sprayed by the removable spray canister device.

19. The method of claim 17, wherein the first liquid product is water.

20. The method of claim 17, wherein the second liquid product comprises one or more of skin protectants, ointments, mineral oil, silicone fluids, dimethicone, cyclomethicone, petrolatum, cod liver oil, lanolin, talc, calamine, kaolin, topical starch, allantoin, barrier materials, zinc oxide, skin moisturizers, skin lotions, moisturizing creams, skin sealants, water, medication, cleaning solutions, moisture barriers, medicaments, a pharmaceutical formulation, and combinations thereof.

21. The method of claim 17 further comprising, moving a bidet assembly using the one or more control units in response to a user input, wherein said spray nozzle assembly, said drying nozzle assembly, and said removable spray canister device are contained in the bidet assembly.

22. The apparatus of claim 1, wherein the bidet assembly further comprises the removable spray canister device.

23. The apparatus of claim 1, wherein the bidet seat further includes a bidet spray cover and a bidet housing cover.

24. The apparatus of claim 23, wherein the bidet housing cover is positioned at a surface of the bidet housing.

25. The apparatus of claim 23, wherein the bidet spray cover is configured to move between an open position and a closed position, and wherein the bidet spray cover covers at least a portion of the bidet assembly when the bidet spray cover is in the closed position.

26. An apparatus for storing a liquid product and spraying the liquid product onto a region of a human body, comprising:
a toilet seat assembly comprising a removable spray canister device, wherein the removable spray canister device is configured to reside in a housing of the toilet seat assembly; and
a first delivery track, wherein the first delivery track is adapted to move the removable spray canister device;
wherein the removable spray canister device is configured to move between a retracted position and an extended position to selectively allow a user to spray the liquid product onto the region of the human body.

27. The apparatus of claim 26, wherein toilet seat assembly further comprises a drying nozzle assembly and a spray nozzle assembly;

wherein the drying nozzle assembly and the spray nozzle assembly each reside in the housing of the toilet seat assembly; and wherein the apparatus further comprises a second delivery track adapted to move the drying nozzle assembly and the spray nozzle assembly.

\* \* \* \* \*